(12) United States Patent
Halpern Chirch et al.

(10) Patent No.: US 10,758,463 B2
(45) Date of Patent: Sep. 1, 2020

(54) HEAT-PROTECTIVE COMPOSITIONS AND METHODS OF USE

(71) Applicant: L'OREAL, Paris (FR)

(72) Inventors: Susan Halpern Chirch, Basking Ridge, NJ (US); Chunhua Li, Hillsborough, NJ (US); Anne-Laure Suzanne Bernard, New York, NY (US); Nicholas David Stebbins, Clark, NJ (US)

(73) Assignee: L'OREAL, Paris (FR)

( * ) Notice: Subject to any disclaimer, the term of this patent is extended or adjusted under 35 U.S.C. 154(b) by 0 days.

(21) Appl. No.: 15/088,559

(22) Filed: Apr. 1, 2016

(65) Prior Publication Data

US 2017/0281489 A1    Oct. 5, 2017

(51) Int. Cl.
| | |
|---|---|
| *A61K 8/26* | (2006.01) |
| *A61K 8/06* | (2006.01) |
| *A61K 8/02* | (2006.01) |
| *A61Q 17/04* | (2006.01) |
| *A61Q 5/00* | (2006.01) |
| *A61K 8/37* | (2006.01) |
| *A61K 8/86* | (2006.01) |
| *A61K 8/34* | (2006.01) |
| *A61K 8/40* | (2006.01) |
| *A61K 8/35* | (2006.01) |

(52) U.S. Cl.
CPC ............... *A61K 8/26* (2013.01); *A61K 8/022* (2013.01); *A61K 8/06* (2013.01); *A61K 8/34* (2013.01); *A61K 8/35* (2013.01); *A61K 8/37* (2013.01); *A61K 8/375* (2013.01); *A61K 8/40* (2013.01); *A61K 8/86* (2013.01); *A61Q 5/00* (2013.01); *A61Q 17/04* (2013.01); *A61K 2800/49* (2013.01); *A61K 2800/524* (2013.01); *A61K 2800/596* (2013.01)

(58) Field of Classification Search
None
See application file for complete search history.

(56) References Cited

U.S. PATENT DOCUMENTS

| | | | |
|---|---|---|---|
| 4,671,955 A | 6/1987 | Palinczar | |
| 4,686,099 A | 8/1987 | Palinczar | |
| 4,710,371 A | 12/1987 | Palinczar | |
| 6,500,411 B2 | 12/2002 | SenGupta et al. | |
| 7,108,860 B2 | 9/2006 | Dueva et al. | |
| 2002/0006419 A1* | 1/2002 | Lorant | A61K 8/06 424/401 |
| 2004/0122152 A1 | 6/2004 | SenGupta et al. | |
| 2004/0161437 A1 | 8/2004 | Bleckmann et al. | |
| 2004/0166178 A1* | 8/2004 | Meybeck | A61K 8/37 424/725 |
| 2004/0170574 A1 | 9/2004 | Bleckmann et al. | |
| 2004/0197279 A1 | 10/2004 | Bleckmann et al. | |
| 2004/0223990 A1* | 11/2004 | Mondet | A61K 8/26 424/401 |
| 2009/0253666 A1 | 10/2009 | Lintner et al. | |
| 2011/0217247 A1 | 9/2011 | Lochhead et al. | |
| 2011/0300572 A1 | 12/2011 | Dueva-Koganov et al. | |
| 2015/0231043 A1 | 8/2015 | Sasaki | |
| 2015/0335543 A1 | 11/2015 | Howell et al. | |
| 2015/0335544 A1 | 11/2015 | Lull et al. | |

FOREIGN PATENT DOCUMENTS

| | | |
|---|---|---|
| DE | 19929475 A1 | 12/2000 |
| EP | 1080713 A2 | 3/2001 |
| EP | 1518533 A2 | 3/2005 |
| EP | 1477159 B1 | 7/2008 |
| FR | 2983719 A1 | 6/2013 |
| GB | 2 404 588 B | 5/2007 |
| WO | WO-0155262 A1 | 8/2001 |
| WO | WO-2013149323 A1 | 10/2013 |

OTHER PUBLICATIONS

D.W. Thompson and J.T. Butterworth, "The Nature of Laponite and Its Aqueous Dispersion" Journal of Colloidal and Interface Science, vol. 151, No. 1, Jun. 1992 (Year: 1992).*
Notification of Transmittal of the International Search Report and the Witten Opinion of the International Search Authority, or the Declaration, International Application No. PCT/US2017/025272.

* cited by examiner

*Primary Examiner* — Nicole P Babson
(74) *Attorney, Agent, or Firm* — Polsinelli PC

(57) ABSTRACT

The present disclosure relates to compositions that protect the skin and hair from extreme heat (external thermal flux). The compositions include: (a) laponite; (b) one or more UV filters; (c) one or more emulsifiers; and (d) water. The compositions are useful in cosmetic, industrial, and military technologies. For instance, the compositions are useful in methods for protecting skin from intense external thermal flux (e.g., fires and explosives). When applied to the hair, the compositions are useful in methods for protecting the hair from heat damage caused by, for example, hair dryers, curling irons, straightening irons, etc.

17 Claims, No Drawings

HEAT-PROTECTIVE COMPOSITIONS AND METHODS OF USE

FIELD OF THE DISCLOSURE

The present disclosure relates to compositions that protect the skin and hair from extreme heat (external thermal flux). The compositions are useful in cosmetic, industrial, and military technologies. For instance, the compositions are useful in methods for protecting skin from intense external thermal flux (e.g., fires and explosives) and for protecting hair from heat damage caused by, for example, hair dryers, curling irons, straightening irons, etc.

BACKGROUND

Skin acts as a natural barrier between the internal and the external environment and therefore plays an important role in vital biological functions such as protection against mechanical and chemical injury, micro-organisms, and ultraviolet damage. Skin, however, is delicate and is easily damaged.

Sunscreens can be used to protect against UV damage but typical sunscreens do not provide protection against intense heat, e.g., fires, explosives, etc. Some occupations exist, such as military and firefighters, in which individuals are exposed to intense thermal fluxes that can cause severe burns to exposed skin. Burns from heat can be prevented by clothing and materials that offer a considerable degree of thermal protection. Protective fire resistant fibers and fabrics or flame resistant treated clothing are critical for firefighters and military personnel that encounter explosives. However, because of ergonomic considerations select areas of the body including the face and the hands may not be covered during operations.

Hair can become seriously damaged when exposed to thermal stresses, such as very high temperatures created by styling devices such as blow driers, curling tongs, and straightening irons. Heat causes the formation of multiple cracks in the cuticle, aligned parallel to the longitudinal axis of the hair fiber (Gamez-Garcia, M. (1998), "The cracking of human hair cuticles by cyclical thermal stresses" Journal of Cosmetic Science 49(3): 141-153). SEM studies have shown that repeated blow drying or use of curling tongs/flat irons can cause articular compression, cuticular disintegration, radial and axial cracking and scale edge chipping (Schweid. B. and G. Martino (2004), "How thermal protection is made possible with sodium polystyrene sulfonate" S.O.F.W.—Journal 130(8): 36-40). Heat exposed hair has also been shown to have a lower dynamic contact angle as cuticle lipids are damaged and removed (Schweid, and Martino (2004).

As described in detail below, the inventors of the instant case discovered compositions that protect the skin and hair from intense heat. Thus, the compositions are useful for protecting the skin and hair from heat and damage caused by heat.

SUMMARY OF THE DISCLOSURE

The instant disclosure relates to compositions that are unique in their ability to protect the skin and hair from external heat (thermal flux). The compositions are useful in cosmetic, industrial, and military technologies. For instance, the compositions are useful in methods for protecting skin from intense external thermal flux (e.g., fires and explosives) and for protecting hair from heat damage caused by, for example, hair dryers, curling irons, straightening irons, etc. The compositions are unique in that they simultaneously protect against heat and UV radiation. The compositions are also unique in that they include a large proportion of water and exhibit a surprising degree of heat protection and heat-resistance.

The heat-protective compositions of the instant disclosure typically include: (a) laponite; (b) optionally, one or more UV filters; (c) optionally, one or more emulsifiers; and (d) water. For example, the heat-protective compositions can include: (a) about 0.1 to about 10 wt. % of laponite; (b) optionally, about 0.1 to about 30 wt. % of UV filter(s); (c) optionally, about 0.1 to about 10 wt. % emulsifier(s); and (d) about 50 to about 95 wt. % water; wherein the weight percentages are based on the total weight of the heat-protective composition; and wherein the heat-protective composition simultaneously protects the skin from both UV radiation and heat.

In some instances, the one or more UV filters are organic UV filters. The UV filter may be a single UV filter, or a combination of two, three, four, five, or more UV filters, including organic and/or inorganic UV filters. In some cases, the total amount of UV filter(s) is from about 1 to about 20 wt. %, based on the total weight of the heat-protective composition.

The appropriate emulsifier(s) often depends on the other components included in the heat-protective compositions. For example, if oils are not included in the compositions, emulsifiers are not necessarily needed. When present, emulsifiers may be nonionic, cationic, anionic, and amphoteric or zwitterionic emulsifiers. In some cases, however, the emulsifier is a nonionic emulsifier such as, for example, a polyol ester, a glycerol ether, an oxyethylenated and/or oxypropylenated ether, and/or an ethylene glycol polymer. Often, the heat-protective composition is in the form of an emulsion.

The heat-protective compositions are useful for protecting the skin and hair from damage caused by heat, and from damage caused by UV radiation.

DETAILED DESCRIPTION OF THE DISCLOSURE

The instant disclosure relates to heat-protective compositions comprising: (a) laponite; (b) optionally, one or more UV filters; (c) optionally, one or more emulsifiers; and (d) water. For example, the heat-protective compositions can include: (a) about 0.1 to about 10 wt. % of laponite; (b) optionally, about 0.1 to about 30 wt. % of one or more UV filters; (c) optionally, about 0.1 to about 10 wt. % of one or more emulsifiers; and (d) about 50 to about 95 wt. % water, wherein the weight percentages are based on the total weight of the heat-protective composition. The heat-protective compositions simultaneously provide protection from both UV radiation and radiant heat.

Laponite is a synthetic sodium magnesium fluorosilicate clay which swells to produce a clear, colorless thixotropic gel when dispersed in water. It is a synthetic layered silicate. As laponites, there may be mentioned in particular the products sold by the company Laporte under the name Laponite XLS, Laponite XLG, Laponite RD, Laponite RDS (these products are silicates of sodium and magnesium and silicates of sodium, lithium and magnesium).

The laponite may have an average particle size of about 5 to about 50 nm, about 10 to about 40 nm, about 15 to about 35 nm, or about 20 to about 30 nm. As mentioned above, the laponite may be in an amount of about 0.1 to about 10 wt. %, based on the total weight of the heat-protective composition. In some instance, the amount of laponite is, however, from about 0.5 to about 10 wt. %, about 1 wt. % to 10 wt. %, about 2 wt. % to about 10 wt. %, about 1 wt. % to about 9 wt. %, about 1 wt. % to about 8 wt. %, or about 2 wt. % to about 8 wt. %.

Many UV filters are known in the art, which may be used in the instant heat-protective compositions. In some cases, the UV filter is one or more organic UV filters. For instance, the organic UV filter may be selected from the group consisting of a para-aminobenzoic acid derivatives, a salicylic derivatives a cinnamic derivative, a benzophenone or an aminobenzophenone, an anthranillic derivative, a β,β -diphenylacrylate derivative, a benzylidenecamphor derivative, a phenylbenzimidazole derivative, a benzotriazole derivative, a triazine derivative, a bisresorcinyl triazine, an imidazoline derivative, a benzalmalonate derivative, a 4,4-diarylbutadiene derivative, a benzoxazole derivative, merocyanine, an amalonitrile or malonate diphenyl butadiene derivative, a chalcone, and a mixture thereof.

As mentioned earlier, the heat-protective compositions of the instant disclosure may include an individual UV filter or a combination of UV filters. For example, heat-protective compositions may include two, three, four, five, or more UV filters. In some cases, the one or more UV filters is in an amount of from about 0.1 to about 25 wt. %, about 0.1 to about 20 wt. %, about 0.1 to about 18 wt. %, 0.1 to about 15 wt. %, about 0.1 to about 12 wt. %, about 0.1 to about 10 wt. %, 0.1 to about 8 wt. %, about 0.1 to about 6 wt. %, about 1 wt. % to about 25 wt. %, about 1 wt. % to about 20 wt. %, about 1 wt. % to about 18 wt. %, about 1 wt. % to about 15 wt. %, about 1 wt. % to about 12 wt. %, about 1 wt. % to about 10 wt. %, about 1 wt. % to about 8 wt. %, about 1 wt. % to about 6 wt. %, about 5 wt. % to about 25 wt. %, about 5 wt. % to about 20 wt. %, about 5 wt. % to about 18 wt. %, about 5 wt % to about 15 wt. %, about 5 wt. % to about 12 wt. %, about 5 wt. % to about 10 wt. %, about 5 wt. % to about 8 wt. %, or from about 3 wt. % to about 20 wt. %, wherein the weight percent is based on the total weight of the heat-protective composition.

The appropriate emulsifier(s) often depends on the other components included in the heat-protective compositions. For example, if oils are not included in the compositions, emulsifiers are not necessarily needed. Thus, in some cases, the compositions of the instant disclosure do not require emulsifier(s). When present, however, the one or more emulsifiers may include, for example, a nonionic emulsifier, a cationic emulsifier, an anionic emulsifier, an amphoteric or zwitterionic emulsifier. In some cases, the emulsifier is a nonionic emulsifier. For example, the nonionic emulsifier may include a compound selected from the group consisting of a polyol ester, a glycerol ether, an oxyethylenated and/or oxypropylenated ether, and/or an ethylene glycol polymer. In some cases, the nonionic emulsifier is a polyol ester and/or an ethylene glycol polymer, for example, a combination of glyceryl stearate and PEG-100 stearate. The type and amount of emulsifier will vary depending on the type of UV filter(s) and other components included in the heat-protective composition. In some cases, the total amount of emulsifier may be from about 0.1 to about 10 wt. %, about 0.1 to about 8 wt. %, about 0.1 to about 6 wt. %, about 0.1 to about 5 wt. %, about 0.1 to about 4 wt. %, about 0.5 to about 10 wt. %, about 0.5 to about 8 wt. %, about 0.5 to about 6 wt. %, about 0.5 to about 5 wt. %, about 1 wt. % to about 10 wt. %, about 1 wt. % to about 8 wt. %, about 1 wt. % to about 6 wt. %, about 1 wt. % to about 5 wt. %, about 2 wt. % to about 10 wt. %, about 2 wt. % to about 8 wt. %, or about 3 wt. % to about 10 wt. %.

The heat-protective composition is often in the form of an emulsion.

The heat-protective compositions described herein may include one or more film formers. For example, the film former may be selected from the group consisting of: sodium silicate, colloidal silica, pullulan, polycacrylate-21 (and) acrylates/dimethylaminoethyl-methacrylate copolymer, polyurethanes, polysaccharides, polyvinylpyrrolidone, acrylates, and a mixture thereof. In some instances, the film former may be an acrylate/octylacrylamide copolymer.

Likewise, in some cases the film former may be selected from the group consisting of polyacrylic acid, polycrotonic acid, polymethacrylic acid, polymaleic acid, polyitaconic acid, octylacrylamide/acrylates/butylaminoethyl methacrylate compolymer, acrylates/octylacrylamide copolymer, acrylates copolymer, octylacrylamide/butylaminoethyl methacrylate copolymer, VA/crotonates/vinyl neodecanoate copolymer, VA/Crotonates copolymer, sodium polystyrene sulfonate, polyurethane-14 (and) AMP-Acrylates copolymer, acrylates/octylacrylamide copolymer, acrylates/steareth-20 itaconate, copolymer, acrylates/ceteth-20 itaconate copolymer, PVM/MA half ethyl ester copolymer, butylated PVP, PVP/hexadecene copolymer, PVP/eicosene copolymer, tricontanyl PVP, butyl ester of PVM/MA copolymer, PVM/MA copolymer, ethyl ester of PVM/MA copolymer, butyl ester of PVM/MA copolymer, vinyl caprolactam/PVP/dimethylaminoethyl methacrylate copolymer, polyquaternium-11, polyquaternium-28, Polyimide-1, PVP-Ninylcaprolactam/DMAPA Acrylates Copolymer, lsobutylene/Ethylmaleimide/Hydroxyethylmaleimide Copolymer, Acrylates/C1-2 Succinates/Hydroxyacrylates Copolymer, PVP/DMAPA Acrylates Copolymer, VP/Acrylates/Lauryl Methacrylate Copolymer, Polyquaternium-55, PVP/Dimethylaminoethylmethacrylate Copolymer, VinylcaprolactamNP/Dimethylaminoethyl Methacrylate Copolymer, VA/Butyl Maleate/Isobornyl Acrylate Copolymer, acrylic acid/ethyl acrylate/t-butyl acrylamide, t-butyl acrylate/ethyl acrylate/methacrylic acid, ethyl acrylate/t-butyl acrylate/methacrylic acid, polyquaternium-16, polyquaternium-16, PVP, PVPNA copolymer, PVPNA copolymer, Polyurethane-1, VP/MethacrylamideNinyl Imidazole Copolymer, Acrylates Copolymer, Acrylates/Acrylamide Copolymer, Polyvinylcaprolactam, Dimethicone/Acrylates Copolymer, Amerchol, acrylic acid/methacrylic acid/acrylates/methacrylates, acrylic acid/methacrylic acid/acrylates/methacrylates/hydroxy ester acrylates; methacryloyl ethyl betaine/acrylates copolymer, Acrylates/Hydroxyesters Acrylates Copolymer, Ethylenecarboxyamide/AMPSA/Methacrylates Copolymer, methacrylic acid/sodium acrylamidomethyl propane sulfonate copolymer, AMP-Acrylates/Allyl Methacrylate Copolymer, Polyacrylates-X, Acrylates/C10-30 Alkyl Acrylates Copolymer, Acrylates Copolymer, Polyurethane-2, Polyurethane-4, PPG-17/IPDI/DMPA Copolymer, polyethylene glycol; water-soluble acrylics; water-soluble polyesters; polyacrylamides; polyamines; polyquaternary amines; styrene maleic anhydride (SMA) resin; or mixtures or combinations thereof.

The heat-protective compositions of the instant disclosure are useful in methods for protecting skin and hair from sun damage; such methods comprise applying the heat-protective composition to the skin or hair. Moreover, due to their unique properties, the heat-protective compositions are particularly useful in methods for simultaneously protecting skin and hair from both UV radiation and from radiant heat; such methods comprising applying a heat-protective composition as described herein to the skin. The methods described herein can further comprise applying at least 2.0 mg/cm² of the heat-protective composition to the skin and maintaining the skin temperature at or below a threshold temperature of 40° C. for at least 10 seconds of exposure to heat flux of 40 kW/m².

The heat-protective compositions typically include about 50 to about 95 wt. % water. In some cases, the composition can include water in an amount of about 55 to about 95 wt. %, about 60 wt. % to about 95 wt. %, about 70 to about 95 wt. %, about 75 to about 95 wt. %, about 50 to about 90 wt. %, about 50 to about 85 wt. % about 50 to about 80 wt. %, about 50 to about 75 wt. % about 50 to about 70 wt. % about 50 to about 65 wt. %, about 60 to 90 wt. %, or about 65 to about 85 wt. %. In some cases, water may be present in lower amounts, for example, in an amount of about 15 to about 50 wt. %, about 20 to about 60 wt. %, about 15 to about 35 wt. %, or about 25 to 50 wt. %.

The instant disclosure relates to methods for boosting SPF of a heat-protective composition comprising UV filters, the method comprising adding laponite to a heat-protective composition comprising UV filters, thereby boosting the SPF of the UV filters. In some instances, the SPF of the heat-protective composition is boosted by at least about 10%, about 20%, about 30%, about 40%, about 50%, about 60%, about 70%, about 80%, about 90%, or higher by addition of laponite to the heat-protective composition (in comparison to an otherwise identical composition without the laponite). In some instance, the SPF of the heat-protective composition is boosted by at least about 2 fold, about 3 fold, about 4 fold, about 5 fold, about 6 fold, about 7 fold by addition of laponite to the heat-protective composition (in comparison to an otherwise identical composition without the laponite).

More exhaustive but non-limiting lists of components useful in the compositions disclosed herein are provided below.

UV Filters

UV filters are well known in the art for their use in stopping UV radiation. For example, the UV filter may be one or more organic UV filters and/or one or more inorganic UV filters. Non-limiting examples of UV filters include:

i. Sparingly soluble UV filters (not appreciably soluble in either water or oil) such as Methylene Bis-Benzotriazolyl Tetramethylbutylphenol, Tris-Biphenyl Triazine, Methanone, 1,1'-(1,4-piperazinediyl)bis[1-[2-[4-(diethylamino)-2-hydroxybenzoyl]phen-yl]- and mixtures thereof.

ii. Oil soluble organic UV filters (at least partially soluble in oil or organic solvent), such as Bis-Ethylhexyloxyphenol Methoxyphenyl Triazine, Butyl Methoxydibenzoylmethane (BMBM), Oxybenzone, Sulisobenzone, Diethylhexyl Butamido Triazone (DBT), Drometrizole Trisiloxane, Ethylhexyl Methoxycinnamate (EHMC), Ethylhexyl Salicylate (EHS), Ethylhexyl Triazone (EHT), Homosalate, Isoamyl p-Methoxycinnamate, 4-Methylbenzylidene Camphor, Octocrylene (OCR), Polysilicone-15, and Diethylamino Hydroxy Benzoyl Hexyl Benzoate (DHHB);

iii. Inorganic UV filters such as titanium oxide and zinc oxide, iron oxide, zirconium oxide and cerium oxide; and iv. Water soluble UV filters such as Phenylbenzimidazole Sulfonic Acid (PBSA), Sulisobenzone-sodium salt, Benzydilene Camphor Sulfonic Acid, Camphor Benzalkonium Methosulfate, Cinoxate, Disodium Phenyl Dibenzylmidazole Tetrasulfonate, Terephthalylidene Dicamphor Sulfonic Acid, PABA, and PEG-25 PABA.

In some instances, the UV filter is one or more of: a para-aminobenzoic acid derivative, a salicylic derivative, a cinnamic derivative, a benzophenone or an aminobenzophenone, an anthranillic derivative, a 3,3-diphenylacrylate derivative, a benzylidenecamphor derivative, a phenylbenzimidazole derivative, a benzotriazole derivative, a triazine derivative, a bisresorcinyl triazine, an imidazoline derivative, a benzalmalonate derivative, a 4,4-diarylbutadiene derivative, a benzoxazole derivative, a merocyanine, malonitrile or a malonate diphenyl butadiene derivative, a chalcone, or a mixture thereof.

Furthermore, combinations of UV filters may be used. For example, the combination of UV filters may be octocrylene, avobenzone (butyl methoxydibenzoylmethane), oxybenzone (benzophenone-3), octisalate (ethylhexyl salicylate), and homosalate, as described in application Ser. No. 13/304,195, which is incorporated herein by reference in its entirety. For instance, this combination of UV filters may be used in the following ratios relative to avobenzone:

the ratio of octocrylene to avobenzone is 1.6:1.0 to 2.4:1.0;
the ratio of oxybenzone to avobenzone 1.0:1.0 to 1.6:1.0;
the ratio of octisalate to avobenzone is 0.8:1.0 to 1.3:1.0; and
the ratio of homosalate to avobenzone is 2.8:1.0 to 4.3:1.

Furthermore, the ratio of each UV filter relative to avobenzone may be about:
2.0:1.0:1.3:1.1:3.6 (octocrylene:avobenzone:oxybenzone:octisalate:homosalate).

In another embodiment, the at least one UV filter is a combination of UV filters comprising octocrylene, avobenzone, octisalate, and homosalate, and optionally oxybenzone, as described in application Ser. No. 13/304,202, which is incorporated herein by reference in its entirety. For instance, this combination of UV filters may be used in the following ratios relative to avobenzone:

the ratio of octocrylene to avobenzone is 1.6:1.0 to 2.4:1.0,
the ratio of oxybenzone to avobenzone 0.0:1.0 to 0.016:1.0,
the ratio of octisalate to avobenzone is 1.3:1.0 to 2.0:1.0, and
the ratio of homosalate to avobenzone is 2.3:1.0 to 3.6:1.

Furthermore, the ratio of each UV filter relative to avobenzone may be about: 2.0:1.0:0.0:1.7:3.0 (octocrylene:avobenzone:oxybenzone:octisalate:homosalate).

In another embodiment, the at least one UV filter is a combination of UV filters comprising octocrylene, butyl methoxydibenzoylmethane, bis-ethylhexyloxyphenol methoxyphenyl triazine, ethylhexyl triazone, terephthalylidene dicamphor sulfonic acid, and drometrizole trisiloxane, as described in application Ser. No. 13/719,328, which is incorporated herein by reference in its entirety. For instance, this combination of UV filters may be used in the following ratios relative to butyl methoxydibenzoylmethane:

the ratio of octocrylene to butyl methoxydibenzoylmethane is 0.8:1.0 to 1.5:1.0;
the ratio of bis-ethylhexyloxyphenol methoxyphenyl triazine to butyl methoxydibenzoylmethane 0.3:1.0 to 0.8:1.0;
the ratio of ethylhexyl triazone to butyl methoxydibenzoylmethane is 0.3:1.0 to 1.0:1.0;
the ratio of terephthalylidene dicamphor sulfonic acid to butyl methoxydibenzoylmethane is 0.1:1.0 to 0.5:1.0; and the ratio of drometrizole trisiloxane to butyl methoxydibenzoylmethane is 0.3:1.0 to 1.0:1.0.

Furthermore, the ratio of each UV filter relative to butyl methoxydibenzoylmethane may be about: 1.2:1.0:0.5:0.6:0.4:0.6 (octocrylene:butyl methoxy-dibenzoylmethane:bis-ethylhexyloxyphenol methoxyphenyl triazine:ethylhexyl triazone:terephthalylidene dicamphor sulfonic acid:drometrizole trisiloxane).

In another embodiment, the at least one UV filter is a combination of UV filters comprising octocrylene, butyl methoxydibenzoylmethane, ethylhexyl triazone, terephthalylidene dicamphor sulfonic acid, and drometrizole trisiloxane, as described in application Ser. No. 13/719,351, which is incorporated herein by reference in its entirety. For instance, this combination of UV filters may be used in the following ratios relative to butyl methoxydibenzoylmethane:

the ratio of octocrylene to butyl methoxydibenzoylmethane is 0.6:1.0 to 1.25:1.0;

the ratio of ethylhexyl triazone to butyl methoxydibenzoylmethane is 0.4:1.0 to 1.0:1.0;

the ratio of terephthalylidene dicamphor sulfonic acid to butyl methoxydibenzoylmethane is 0.3:1.0 to 0.7:1.0; and the ratio of drometrizole trisiloxane to butyl methoxydibenzoylmethane is 0.4:1.0 to 1.1:1.0.

Furthermore, the ratio of each UV filter relative to butyl methoxydibenzoylmethane may be about: 1.0:1.0:0.7:0.5:0.7 (octocrylene:butyl methoxydibenzoylmethane:ethylhexyl triazone:terephthalylidene dicamphor sulfonic acid:drometrizole trisiloxane).

In another embodiment, the at least one UV filter is a combination of UV filters comprising octocrylene, butyl methoxydibenzoylmethane, bis-ethylhexyloxyphenol methoxyphenyl triazine, terephthalylidene dicamphor sulfonic acid, and drometrizole trisiloxane, as described in application Ser. No. 13/719,368, which is incorporated herein by reference in its entirety. For instance, this combination of UV filters may be used in the following ratios relative to butyl methoxydibenzoylmethane:

the ratio of octocrylene to butyl methoxydibenzoylmethane is 0.8:1.0 to 1.2:1.0;

the ratio of bis-ethylhexyloxyphenol methoxyphenyl triazine to butyl methoxydibenzoylmethane is 0.2:1.0 to 0.6:1.0;

the ratio of terephthalylidene dicamphor sulfonic acid to butyl methoxydibenzoylmethane is 0.0.25:1.0 to 0.75:1.0; and the ratio of drometrizole trisiloxane to butyl methoxydibenzoylmethane is 0.4:1.0 to 0.8:1.0.

Furthermore, the ratio of each UV filter relative to butyl methoxydibenzoylmethane may be about: 1.0:1.0:0.4:0.4:0.6 (octocrylene:butyl methoxydibenzoylmethane:bis-ethylhexyloxyphenol methoxyphenyl triazine:terephthalylidene dicamphor sulfonic acid:drometrizole trisiloxane).

In another embodiment, the at least one UV filter is a combination of UV filters comprising octocrylene, butyl methoxydibenzoylmethane, bis-ethylhexyloxyphenol methoxyphenyl triazine, terephthalylidene dicamphor sulfonic acid, and drometrizole trisiloxane, as described in application Ser. No. 13/719,374, which is incorporated herein by reference in its entirety. For instance, this combination of UV filters may be used in the following ratios relative to butyl methoxydibenzoylmethane is as follows:

the ratio of octocrylene to butyl methoxydibenzoylmethane is 0.8:1.0 to 1.3:1.0;

the ratio of bis-ethylhexyloxyphenol methoxyphenyl triazine to butyl methoxydibenzoylmethane is 0.1:1.0 to 0.6:1.0;

the ratio of ethylhexyl triazone to butyl methoxydibenzoylmethane is 0.2:1.0 to 0.6:1.0; and the ratio of drometrizole trisiloxane to butyl methoxydibenzoylmethane is 0.3:1.0 to 0.7:1.0. [Synergistic combination from PR2012573]

Furthermore, the ratio of each UV filter relative to butyl methoxydibenzoylmethane may be about: 1.0:1.0:0.3:0.5:0.5 (octocrylene:butyl methoxydibenzoylmethane:bis-ethylhexyloxyphenol methoxyphenyl triazine:ethylhexyl triazone:drometrizole trisiloxane).

In another embodiment, the at least one UV filter is a combination of UV filters comprising octocrylene, butyl methoxydibenzoylmethane, bis-ethylhexyloxyphenol methoxyphenyl triazine, terephthalylidene dicamphor sulfonic acid, and terephthalylidene dicampohor sulfonic acid, as described in application Ser. No. 13/719,393, which is incorporated herein by reference in its entirety. For instance, this combination of UV filters may be used in the following ratios relative to butyl methoxydibenzoylmethane is as follows:

the ratio of octocrylene to butyl methoxydibenzoylmethane is 0.8:1.0 to 1.6:1.0;

the ratio of bis-ethylhexyloxyphenol methoxyphenyl triazine to butyl methoxydibenzoylmethane is 0.2:1.0 to 0.6:1.0;

the ratio of ethylhexyl triazone to butyl methoxydibenzoylmethane is 0.3:1.0 to 0.6:1.0; and the ratio of terephthalylidene dicampohor sulfonic acid to butyl methoxydibenzoylmethane is 0.01:1.0 to 0.3:1.0.

Furthermore, the ratio of each UV filter relative to butyl methoxydibenzoylmethane may be about: 1.2:1.0:0.3:0.5:0.1 (octocrylene:butyl methoxydibenzoylmethane:bis-ethylhexyloxyphenol methoxyphenyl triazine:ethylhexyl triazone:terephthalylidene dicampohor sulfonic acid).

Emulsifiers

Emulsifiers are well known in the art and include amphoteric, anionic, cationic or nonionic emulsifiers, used alone or as a mixture, and optionally with a co-emulsifier. The emulsifiers are chosen in an appropriate manner according to the emulsion to be obtained.

For W/O emulsions, examples of emulsifiers that may be mentioned include dimethicone copolyols, such as the mixture of cyclomethicone and dimethicone copolyol sold under the trade name DC 5225 C by the company Dow Corning, and alkyl dimethicone copolyols such as the lauryl dimethicone copolyol sold under the name Dow Corning 5200 Formulation Aid by the company Dow Corning, and the cetyl dimethicone copolyol sold under the name Abil EM 90™ by the company Goldschmidt.

For O/W emulsions, examples of emulsifiers that may be mentioned include nonionic emulsifiers such as oxyalkylenated (more particularly polyoxyethylenated) fatty acid esters of glycerol; oxyalkylenated fatty acid esters of sorbitan; oxyalkylenated (oxyethylenated and/or oxypropylenated) fatty acid esters; oxyalkylenated (oxyethylenated and/or oxypropylenated) fatty alcohol ethers; sugar esters such as sucrose stearate; and mixtures thereof.

In some instance, the one or more emulsifiers include an organosiloxane emulsifier, including crosslinked organosiloxane emulsifiers. For example, the compositions may comprise one or more crosslinked organosiloxane emulsifier selected from the group consisting of dimethicone/dimethicone PEG/PPG 15 crosspolymer, dimethicone PEG-10 crosspolymer, dimethicone PEG-10/15 crosspolymer, dimethicone PEG-15 crosspolymer, dimethicone polyglycerin-3 crosspolymer, dimethicone PPG-20 crosspolymer, dimethiconol/methylsilanol/silicate crosspolymer; dimethiconol/silicate crosspolymer, lauryl dimethicone PEG-15 crosspolymer, lauryl dimethicone polyglycerin-3 crosspolymer, PEG-8 dimethicone polysorbate-20 crosspolymer, PEG-10 dimethicone/vinyl dimethicone crosspolymer, PEG-10 lauryl dimethicone crosspolymer, PEG-15/lauryl dimethicone crosspolymer, PEG-15 laurylpolydimethylsiloxyethyl crosspolymer.

In another embodiment, the compositions include one or more linear organosiloxane emulsifier selected from the group consisting of cyclotetrasiloxane (and) cyclopentasiloxane (and) PEG/PPG-18 dimethicone, cyclopentasiloxane (and) PEG/PPG-18/18 dimethicone; PEG/PPG-18/18 dimethicone; lauryl PEG/PPG-18/18 methicone; cetyl PEG/PPG-14/14 dimethicone; bis-cetyl PEG/PPG-14/14 dimethicone; cetyl PEG/PPG-10/1 dimethicone; PEG-11 methyl ether dimethicone; PEG/PPG-20/22 butyl ether dimethicone; PEG-9 dimethicone; PEG-3 dimethicone; PEG-9 methyl ether dimethicone; PEG-10 dimethicone; lauryl PEG-9 polydimethylsiloxyethyl dimethicone.

Usable oxyalkylenated organosiloxane emulsifier include the following:

An oxyalkylenated organosiloxane emulsifier having the general formula:

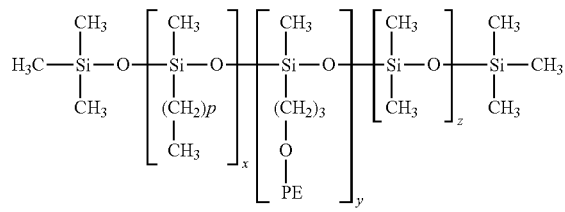

wherein p is 0-40 (the range including all numbers between and subranges such as 2, 3, 4, 13, 14, 15, 16, 17, 18, etc.), and PE is $(-C_2H_4O)_a-(-C_3H_6O)_b-H$ wherein a is 0-25, b is 0-25 with the proviso that both a and b cannot be 0 simultaneously, x, y, and z are each independently ranging from 0 to 1 million with the proviso that x and y cannot be 0 simultaneously. In some cases, x, y, z, a, and b are such that the molecular weight of the polymer ranges from about 5,000 to about 500,000, from about 10,000 to 100,000, or is about 50,000, and the polymer is generically referred to as dimethicone copolyol. In some instances, p is such that the long chain alkyl is cetyl or lauryl, and the the compound is called, generically, cetyl dimethicone copolyol or lauryl dimethicone copolyol respectively. In some cases the number of repeating ethylene oxide or propylene oxide units in the polymer are also specified, such as a dimethicone copolyol that is also referred to as PEG-15/PPG-10 dimethicone, which refers to a dimethicone having substituents containing 15 ethylene glycol units and 10 propylene glycol units on the siloxane backbone. It is also possible for one or more of the methyl groups in the above general structure to be substituted with a longer chain alkyl (e.g. ethyl, propyl, butyl, etc.) or ether, such as methyl ether, ethyl ether, propyl ether, butyl ether, and the like.

An oxyalkylenated organosiloxane emulsifier having the general formula:

wherein each n is independently 0-100 with the proviso that there must be at least one PE radical. In some instances, where each n independently ranges from about 2 to 30, and PE $(-C_2H_4O)_a-(-C_3H_6O)_b-H$ wherein a is 0-25, b is 0-25 with the proviso that both a and b cannot simultaneously be 0; and wherein w, x, y, and z are each independently 0 to 1,000,000 with the proviso that there is at least one PE. In some embodiments the organosiloxane emulsifier is lauryl PEG-9 Polydimethylsiloxyethyl Dimethicone. Oxyalkylenated organosiloxane emulsifiers disclosed in U.S. Pat. No. 9,095,543 are useful in the instant compositions. U.S. Pat. No. 9,095,543 is incorporated herein by reference in its entirety.

Further examples of organosiloxane emulsifiers include those having C.T.F.A. names Bis-Butyldimethicone Polyglyceryl-3; Bis-PEG/PPG-14/14 Dimethicone; Bis-butyldimethicone Polyglyceryl-3; Bis-isobutyl PEG/PPG-10/7 Dimethicone copolymer; Bis-PEG/PPG-18/6 Dimethicone; Bis-PEG/PPG-20/20 Dimethicone; Bis-PEG/PPG-16/16 PEG/PPG-16/16 Dimethicone; Bis(PPG-7 Undeceneth-21-Dimethicone; Cetyl Dimethicone PEG-7 Acetate; Cetyl PEG-8 Dimethicone; Cetyl PEG/PPG-15/16 Butyl Ether Dimethicone; Cetyl PEG/PPG-15/15 Butyl Ether Dimethicone; Cetyl PEG/PPG-7/3 Dimethicone; Cetyl PEG/PPG-10/1 Dimethicone; Dimethicone PEG-15 Acetate; Dimethicone PEG-7 Cocoate; Dimethicone PEG-7 Phosphate; Dimethicone PEG-10 Phosphate; Dimethicone PEG/PPG-7/4 Phosphate; Dimethicone PEG/PPG-12/4 Phosphate; Dimethicone PEG-7 Undecylenate; Lauryl Dimethicone PEG-10 Phosphate; Isopolyglyceryl-3 Dimethicone; Isopolyglyceryl-3 Dimethiconol; Isostearyl Carboxyldecyl PEG-8 Dimethicone; Lauryl Methicone PEG-10 Phosphate; Lauryl PEG-8 Dimethicone; Lauryl PEG-10 Methyl Ether Dimethicone; Lauryl PEG/PPG-18/18 Methicone; PEG-6 Methyl Ether Dimethicone; PEG-7 Methyl Ether Dimethicone; PEG-9 Methyl Ether Dimethicone; PEG-10 Methyl Ether Dimethicone; PEG-11 Methyl Ether Dimethicone; PEG-11 Methyl Ether Dimethicone; PEG-32 Methyl Ether Dimethicone; PEG-PEG/PPG-28/21 Acetate Dimethicone; PEG/PPG-22/22 Butyl Ether Dimethicone; PEG/PPG-23/23 Butyl Ether Dimethicone; PEG/PPG-24/18 Butyl Ether Dimethicone; PEG/PPG-3/10 Dimethicone; PEG/PPG-4/12 Dimethicone; PEG/PPG-6/11 Dimethicone; PEG/PPG-8/14 Dimethicone; PEG/PPG-12/16 Dimethicone; PEG/PPG-12/18 Dimethicone; PEG/PPG-14/4 Dimethicone; PEG/PPG-15/5 Dimethicone; PEG/PPG-15/15 Dimethicone; PEG/PPG-16/2 Dimethicone; PEG/PPG-16/8 Dimethicone; PEG/PPG-17/18 Dimethicone; PEG/PPG-18/12 Dimethicone; PEG/PPG-19/19 Dimethicone; PEG/PPG-20/6 Dimethicone; PEG/PPG-20/15 Dimethicone; PEG/PPG-20/20 Dimethicone; PEG/PPG-20/29 Dimethicone; PEG/PPG-22/23 Dimethicone; PEG/PPG-22/24 Dimethicone; PEG/PPG-25/25 Dimethicone; PEG/PPG-27/27 Dimethicone; PEG/PPG-30/10 Dimethicone; PEG/PPG-10/3 Oleyl Ether Dimethicone; PEG-8 trisiloxane; Polyglyceryl-3 Polydim-

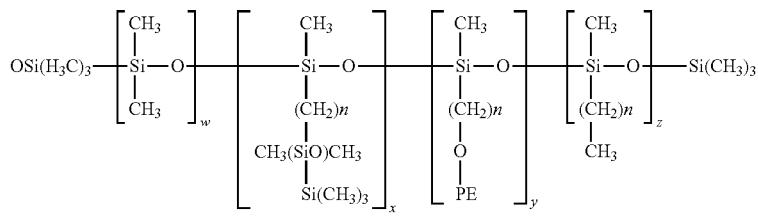

ethylsiloxyethyl Dimethicone; PPG-12 Butyl Ether Dimethicone; Silicone Quaternium-17; TEA-Dimethicone PEG-7 Phosphate; or mixtures thereof.

Further examples of commercial linear organosiloxane emulsifiers are those sold by Dow Corning under the tradename Dow Corning 3225C Formulation Aid having the CTFA name cyclotetrasiloxane (and) cyclopentasiloxane (and) PEG/PPG-18 dimethicone; or 5225C Formulation Aid, having the CTFA name cyclopentasiloxane (and) PEG/PPG-18/18 dimethicone; or Dow Corning 190 Surfactant having the CTFA name PEG/PPG-18/18 dimethicone; or Dow Corning 193 Fluid, Dow Corning 5200 having the CTFA name lauryl PEG/PPG-18/18 methicone; or Abil EM 90 having the CTFA name cetyl PEG/PPG-14/14 dimethicone sold by Goldschmidt; or Abil EM 97 having the CTFA name bis-cetyl PEG/PPG-14/14 dimethicone sold by Goldschmidt; or Abil WE 09 having the CTFA name cetyl PEG/PPG-10/1 dimethicone in a mixture also containing polyglyceryl-4 isostearate and hexyl laurate; or KF-6011 sold by Shin-Etsu Silicones having the CTFA name PEG-11 methyl ether dimethicone; KF-6012 sold by Shin-Etsu Silicones having the CTFA name PEG/PPG-20/22 butyl ether dimethicone; or KF-6013 sold by Shin-Etsu Silicones having the CTFA name PEG-9 dimethicone; or KF-6015 sold by Shin-Etsu Silicones having the CTFA name PEG-3 dimethicone; or KF-6016 sold by Shin-Etsu Silicones having the CTFA name PEG-9 methyl ether dimethicone; or KF-6017 sold by Shin-Etsu Silicones having the CTFA name PEG-10 dimethicone; or KF-6038 sold by Shin-Etsu Silicones having the CTFA name lauryl PEG-9 polydimethylsiloxyethyl dimethicone.

Also suitable are various types of fully or partially crosslinked oxyalkylenated organosiloxane emulsifiers. They may be elastomeric or non-elastomeric. They are sometimes referred to as "emulsifying elastomers" because of they have both elastomeric and emulsifying properties.

Polyoxyalkylenated silicone elastomers that may be used in at least one embodiment include those sold by Shin-Etsu Silicones under the names KSG-21, KSG-20, KSG-30, KSG-31, KSG-32, KSG-33; KSG-210 which is dimethicone/PEG-10/15 crosspolymer dispersed in dimethicone; KSG-310 which is PEG-15 lauryl dimethicone crosspolymer; KSG-320 which is PEG-15 lauryl dimethicone crosspolymer dispersed in isododecane; KSG-330 (the former dispersed in triethylhexanoin), KSG-340 which is a mixture of PEG-10 lauryl dimethicone crosspolymer and PEG-15 lauryl dimethicone crosspolymer.

Also suitable are polyglycerolated silicone elastomers include dimethicone/polyglycerin-3 crosspolymer dispersed in dimethicone; or lauryl dimethicone/polyglycerin-3 crosspolymer dispersed in a variety of solvent such as isododecane, dimethicone, triethylhexanoin, sold under the Shin-Etsu tradenames KSG-810, KSG-820, KSG-830, or KSG-840. Also suitable are silicones sold by Dow Corning under the tradenames 9010 and DC9011.

Further examples of crosslinked organosiloxane emulsifiers include, but are not limited to Dimethicone/dimethicone PEG/PPG 15 crosspolymer; Dimethicone PEG-10 crosspolymer; Dimethicone PEG-10/15 Crosspolymer; Dimethicone PEG-15 Crosspolymer; Dimethicone Polyglycerin-3 Crosspolymer; Dimethicone PPG-20 Crosspolymer; Dimethiconol/Methylsilanol/Silicate Crosspolymer; Dimethiconol/Silicate Crosspolymer; Lauryl Dimethicone PEG-15 Crosspolymer; Lauryl Dimethicone Polyglycerin-3 Crosspolymer; PEG-8 Dimethicone Polysorbate-20 Crosspolymer; PEG-10 DimethiconeNinyl Dimethicone Crosspolymer; PEG-10 Lauryl Dimethicone Crosspolymer; PEG-15/Lauryl Dimethicone Crosspolymer; and PEG-15 Laurylpolydimethylsiloxyethyl Crosspolymer.

Film Formers

Film-formers may be incorporated into the compositions to ensure even coverage and improved water resistance. The film former is typically a hydrophobic material that imparts film forming and/or waterproofing characteristics. One such agent is polyethylene, which is available from New Phase Technologies as Performalene® 400, a polyethylene having a molecular weight of 400. Another suitable film former is polyethylene 2000 (molecular weight of 2000), which is available from New Phase Technologies as Performalene®. Yet, another suitable film former is synthetic wax, also available from New Phase Technologies as Performa® V-825. Other typical film-formers include acrylates/acrylamide copolymer, acrylates copolymer, acrylates/$C_{12}$-$C_{22}$ alkylmethacrylate copolymer, polyethylene, waxes, VP/dimethiconylacrylate/polycarbamylpolyglycol ester, butylated PVP, PVP/hexadecene copolymer, octadecene/MA copolymer, PVP/eicosene copolymer, tricontanyl PVP, *Brassica Campestris/Aleuritis* Fordi Oil copolymer, decamethyl cyclopentasiloxane (and) trimethylsiloxysilicate, and mixtures thereof. In some cases, the film former is acrylates/$C_{12}$-$C_{22}$ alkylmethacrylate copolymer sold under the tradename Allianz OPT® by ISP.

Many of the common film-forming polymers included in heat-protective compositions are not soluble in ethanol (such as PVP/Eicosene copolymer). A common film-former employed in ethanol based sunscreen products is Dermacryl LT or Dermacryl 79 marketed by Akzo Nobel (INCI Name: acrylates/octylacrylamide copolymner). Dermacryl LT (CAS Number: 80570-62-3) is a hydrophobic, high molecular weight carboxylated acrylic copolymer. It functions as a film-former in a broad range of formulations, imparting waterproofing, increased occlusivity and decreased rub-off of actives.

The at least one film former may be, for example, sodium silicate, colloidal silica, pullulan, polycacrylate-21 (and) acrylates/dimethylaminoethylmethacrylate copolymer, polyurethanes, polysaccharides, polyvinylpyrrolidone, polyacrylates, acrylate copolymers, and the mixtures thereof. In some cases, the at least one film former comprises a polysaccharide, which may have one or more free hydroxyl groups. Furthermore, in some cases, the polysaccharide is pullulan. In some cases, the composition comprises at least two film formers, which may be any two film formers, e.g., sodium silicate and pullulan.

Non-limiting examples of film formers useable herein include: acrylic acid, crotonic acid, methacrylic acid, maleic acid, itaconic acid and combinations and mixtures thereof. Additional film forming polymers, either synthetic or natural can be used with the acid containing polymers described above. Non-limiting examples of these additional film forming polymers are: from National Starch and Chemical Company, AMPHOMER®. and AMPHOMER® LV-71 polymers (octylacrylamide/acrylates/butylaminoethyl methacrylate copolymer), AMPHOMER® HC polymer (acrylates/octylacrylamide copolymer) BALANCE® 0/55 and BALANCE® CR polymers (acrylates copolymer), BALANCE® 47 polymer (octylacrylamide/butylaminoethyl methacrylate copolymer), RESYN® 28-2930 polymer (VA/crotonates/vinyl neodecanoate copolymer), RESYN® 28-1310 polymer (VA/Crotonates copolymer), FLEXAN® polymers (sodium polystyrene sulfonate), DynamX polymer (polyurethane-14 (and) AMP-Acrylates copolymer), RESYN® XP polymer (acrylates/octylacrylamide copolymer), STRUCTURE® 2001 (acrylates/stearth-20 itaconate copolymer) and STRUCTURE® 3001 (acrylates/ceteth-20 itaconate copolymer); from ISP, OMNIREZ-2000® (PVM/MA half ethyl ester copolymer), GANEX P-904® (butylated PVP), GANEX V-216® (PVP/hexadecene copolymer) GANEX® V-220 (PVP/eicosene copolymer), GANEX® WP-660 (tricontanyl PVP), GANTREZ® A425 (butyl ester of PVM/MA copolymer), GANTREZ® AN-119 PVM/MA copolymer, GANTREZ® ES 225 (ethyl ester of PVM/MA copolymer), GANTREZ® ES425 (butyl ester of PVM/MA copolymer), GAFFIX® VC-713 (vinyl caprolactam/PVP/dimethylaminoethyl methacrylate copolymer), GAFQUAT® 755 (polyquaternium-11), GAFQUAT HS-100® (polyquaternium-28) AQUAFLEX® XL-30 (Polyimide-1), AQUAFLEX® SP-40 (PVP/Vinylcaprolactam/DMAPA Acrylates Copolymer), AQUAFLEX® PX-64 (Isobutylene/Ethylmaleimide/Hydroxethylmaleimide Copolymer), ALLIANZ® LT-120 (Acrylates/C1-2 Succinates/Hydroxyacrylates Copolymer), STYLEZE® CC-10 (PVP/DMAPA Acrylates Copolymer), STYLEZE® 2000 (VP/Acrylates/Lauryl Methacrylate Copolymer), STYLEZE® W-20 (Polyquaternium-55), Copolymer Series (PVP/Dimethylaminoethylmethacrylate Copolymer), ADVANTAGE® S and ADVANTAGE® LCA (VinylcaprolactamNP/Dimethylaminoethyl Methacrylate Copolymer), ADVANTAGE® PLUS (VA/Butyl Maleate/Isobornyl Acrylate Copolymer); from BASF, ULTRAHOLD STRONG (acrylic acid/ethyl acrylate/t-butyl acrylamide), LUVIMER® 100P (t-butyl acrylate/ethyl acrylate/methacrylic acid), LUVIMER® 36D (ethyl acrylate/t-butyl acrylate/methacrylic acid), LUVIQUAT® HM-552 (polyquaternium-16), LUVIQUAT® HOLD (polyquaternium-16); LUVISKOL® K30 (PVP) LUVISKOL® K90 (PVP), LUVISKOL® VA 64 (PVP/VA copolymer) LUVISKOL® VA73W (PVP/VA copolymer), LUVISKOL® VA, LUVISET® PUR (Polyurethane-1), LUVISET® Clear (VP/MethacrylamideNinyl Imidazole Copolymer), LUVIFLEX® SOFT (Acrylates Copolymer), ULTRAHOLD® 8 (Acrylates/Acrylamide Copolymer), LUVISKOL® Plus (Polyvinylcaprolactam), LUVIFLEX® Silk (PEG/PPG-25/25 Dimethicone/Acrylates Copolymer); From Amerchol, AMERHOLD® DR-25 (acrylic acid/methacrylic acidlacrylates/methacrylates); from Rohm&Haas, ACUDYNE® 258 (acrylic acid/methacrylic acid/acrylates/methacrylates/hydroxy ester acrylates; from Mitsubishi and distributed by Clariant, DIAFORMER® Z-301, DIAFORMER® Z-SM, and DIAFORMER® Z-400 (methacryloyl ethyl betaine/acrylates copolymer), ACUDYNE® 180 (Acrylates/Hydroxyesters Acrylates Copolymer), ACUDYNE® SCP (Ethylenecarboxyamide/AMPSA/Methacrylates Copolymer), and the ACCLTLYN® rheological modifiers; from ONDEO Nalco, FIXOMER® A-30 and FIXOMER® N-28 (INCI names: methacrylic acid/sodium acrylamidomethyl propane sulfonate copolymer); from Noveon, FIXATE® G-100 (AMP-Acrylates/Allyl Methacrylate Copolymer), FIXATE PLUS® (Polyacrylates-X), CARBOPOL® Ultrez 10 (Carbomer), CARBOPOL® Ultrez 20 (Acrylates/C10-30 Alkyl Acrylates Copolymer), AVALURE® AC series (Acrylates Copolymer), AVALURE® UR series (Polyurethane-2, Polyurethane-4, PPG-17/IPDI/DMPA Copolymer) polyethylene glycol; water-soluble acrylics; water-soluble polyesters; polyacrylamides; polyamines; polyquaternary amines; styrene maleic anhydride; (SMA) resin; polyethylene amine; and other conventional polymer that is polar solvent soluble or that can be made soluble through neutralization with the appropriate base.

Typically, the at least one film former is present in an amount from about 1% to about 20%, about 1% to about 18%, about 1% to about 16%, about 1% to about 14%, about 1% to about 12%, about 1% to about 10%, about 1% to about 8%, about 2% to about 20%, about 2% to about 18%, about 2% to about 16%, about 2% to about 16%, about 2% to about 14%, about 2% to about 12%, about 2% to about 10%, about 2% to about 8%, about 3% to about 20%, about 3% to about 18%, about 3% to about 16%, about 3% to about 14%, about 3% to about 12%, about 3% to about 10%, about 3% to about 8%, about 4% to about 20%, about 4% to about 18%, about 4% to about %, about 4% to about 14%, about 4% to about 14%, about 4% to about 12%, about 4% to about 10%, about 4% to about 8%, about 5% to about 20%, about 5% to about 18%, about 5% to about 16%, about 5% to about 14%, about 5% to about 12%, about 5% to about 10%, about 5% to about 8%, or about 3% to about 15%, by weight of the total weight of the composition.

Oils

The compositions may include one or more oils, for example, silicone oils, fluoro oils, hydrocarbon-based oils, etc. The term "oil" means any fatty substance which is in liquid form at room temperature (20-25° C.) and at atmospheric pressure (760 mmHg). Often, at least one of the oils in the composition is part of an oily phase. An "oily phase" is a phase comprising at least one oil that may include additional liposoluble and lipophilic ingredients and the fatty substances. The oily phase can be combined with an aqueous phase in an emulsion. Oil that is suitable for use herein may be volatile or non-volatile. The term "volatile oil" relates to oil that is capable of evaporating on contact with the skin or a keratin fiber in less than one hour, at room temperature and atmospheric pressure. The volatile oil(s) are liquid at room temperature and have a non-zero vapor pressure, at room temperature and atmospheric pressure, ranging in particular from 0.13 Pa to 40 000 Pa ($10^{-3}$ to 300 mmHg). The term "non-volatile oil" relates to oil which remains on the skin or the keratin fiber, at room temperature and atmospheric pressure, for at least several hours and which in particular has a vapor pressure of less than $10^{-3}$ mmHg (0.13 Pa).

The term "silicone oil" relates to oil comprising at least one silicon atom, and especially at least one Si—O group. The term "fluoro oil" relates to oil comprising at least one fluorine atom. The term "hydrocarbon-based oil" relates to oil comprising mainly hydrogen and carbon atoms. Hydrocarbon-based oil may be animal hydrocarbon-based oil, plant hydrocarbon-based oil, mineral hydrocarbon-based oil or a synthetic hydrocarbon-based oil. Further, suitable oil may be a mineral hydrocarbon-based oil, a plant hydrocarbon-based oil, or a synthetic hydrocarbon-based oil.

Silicone Oils

The compositions described herein may comprise one or more silicone oils. Non-limiting examples of silicone oils include dimethicone, cyclomethicone, polysilicone-11, phenyl trimethicone, trimethylsilylamodimethicone, and stearoxytrimethylsilane. In some cases, the composition includes dimethicone, and optionally additional oils, including additional silicone oils. Typically, the one or more silicone oils is a non-volatile silicon oil. In some embodiments, the silicone oil is polydimethylsiloxanes (PDMSs), polydimethylsiloxanes comprising alkyl or alkoxy groups which are pendent and/or at the end of the silicone chain, which groups each contain from 2 to 24 carbon atoms, or phenyl silicones, such as phenyl trimethicones, phenyl dimethicones, phenyl (trimethylsiloxy)diphenylsiloxanes, diphenyl dimethicones, diphenyl(methyldiphenyl)trisiloxanes or (2-phenylethyl) trimethylsiloxysilicates.

Other examples of silicone oils that may be mentioned include volatile linear or cyclic silicone oils, especially those with a viscosity 8 centistokes ($8 \times 10^6$ m²/s) and especially containing from 2 to 7 silicon atoms, these silicones optionally comprising alkyl or alkoxy groups containing from 1 to 10 carbon atoms. As volatile silicone oils that may be used in the disclosure, mention may be made especially of octamethylcyclotetrasiloxane, decamethylcyclopentasiloxane, dodecamethylcyclohexasiloxane, heptamethylhexyltrisiloxane, heptamethyloctyltrisiloxane, hexamethyldisiloxane, octamethyltrisiloxane, decamethyltetrasiloxane and dodecamethylpentasiloxane, and mixtures thereof.

Fluoro Oils

The compositions described herein may comprise one or more fluoro oils. For example, the one or more fluoro oil may be selected from the group consisting of perfluoromethylcyclopentane, perfluoro-1,3-dimethylcyclohexane, dodecafluoropentane, tetradecafluorohexane, bromoperfluorooctyl, nonafluoromethoxybutane, nonafluoroethoxyisobutane and 4-trifluoromethylperfluoromorpholine. Volatile fluoro oils, such as nonafluoromethoxybutane, decafluoropentane, tetradecafluorohexane, dodecafluoropentane, may also be used.

Hydrocarbon-Based Oils

The compositions described herein may comprise one or more hydrocarbon-based oils. For example, the hydrocarbon-based oil may be a saturated hydrocarbon, an unsaturated hydrocarbon, lipids, triglycerides, a natural oil, and/or a synthetic oil. In some embodiments, the compositions include a synthetic oil selected from the group consisting of hydrogenated polyisobutene and hydrogenated polydecene.

The hydrocarbon-based oil may be a non-volatile hydrocarbon-based, such as:

(i) hydrocarbon-based oils of plant origin, such as glyceride triesters, which are generally triesters of fatty acids and of glycerol, the fatty acids of which can have varied chain lengths from $C_4$ to $C_{24}$, it being possible for these chains to be saturated or unsaturated and linear or branched; these oils are in particular wheat germ oil, sunflower oil, grape seed oil, sesame oil, corn oil, apricot oil, castor oil, shea oil, avocado oil, olive oil, soybean oil, sweet almond oil, palm oil, rapeseed oil, cottonseed oil, hazelnut oil, macadamia oil, jojoba oil, alfalfa oil, poppy oil, pumpkin seed oil, marrow oil, blackcurrant oil, evening primrose oil, millet oil, barley oil, quinoa oil, rye oil, safflower oil, candlenut oil, passionflower oil, and musk rose oil.

(ii) synthetic ethers containing from 10 to 40 carbon atoms;

(iii) linear or branched hydrocarbons of mineral or synthetic origin, such as petroleum jelly, polydecenes, hydrogenated polyisobutene such as Parleam, and 4 0 squalane;

(iv) synthetic esters, for instance oils of formula RCOOR' in which R represents a linear or branched fatty acid residue containing from 1 to 40 carbon atoms and R' represents a hydrocarbon-based chain that is especially branched, containing from 1 to 40 carbon atoms on condition that R+R' is ≥10, for instance Purcellin oil (cetearyl octanoate), isopropyl myristate, isopropyl palmitate, $C_{12}$-$C_{15}$ alkyl benzoate, such as the product sold under the trade name Finsolv TN® or Witconol TN® by Witco or Tegosoft TN® by Evonik Goldschmidt, 2-ethylphenyl benzoate, such as the commercial product sold under the name X-Tend 226 by ISP, isopropyl lanolate, hexyl laurate, diisopropyl adipate, isononyl isononanoate, oleyl erucate, 2-ethylhexyl palmitate, isostearyl isostearate, diisopropyl sebacate, such as the product sold under the name of "Dub Dis" by Stearinerie Dubois, octanoates, decanoates or ricinoleates of alcohols or polyalcohols, such as propylene glycol dioctanoate; hydroxylated esters, such as isostearyl lactate or diisostearyl malate; and pentaerythritol esters; citrates or tartrates, such as di(linear $C_{12}$-$C_{13}$ alkyl) tartrates, such as those sold under the name Cosmacol ETI® by Enichem Augusta Industriale, and also di(linear $C_{14}$-$C_{15}$ alkyl) tartrates, such as those sold under the name Cosmacol ETL® by the same company; or acetates;

(v) fatty alcohols that are liquid at room temperature, containing a branched and/or unsaturated carbon-based chain containing from 12 to 26 carbon atoms, for instance octyldodecanol, isostearyl alcohol, oleyl alcohol, 2-hexyldecanol, 2-butyloctanol or 2-undecylpentadecanol;

(vi) higher fatty acids, such as oleic acid, linoleic acid or linolenic acid;

(vii) carbonates, such as dicaprylyl carbonate, such as the product sold under the name Cetiol CC® by Cognis;

(viii) fatty amides, such as isopropyl N-lauroyl sarcosinate, such as the product sold under the trade name Eldew SL 205® from Ajinomoto; and (ix) essential oils selected from the group consisting of sunflower oil, sesame oil, peppermint oil, macadamia nut oil, tea tree oil, evening primrose oil, sage oil, rosemary oil, coriander oil, thyme oil, pimento berries oil, rose oil, anise oil, balsam oil, bergamot oil, rosewood oil, cedar oil, chamomile oil, sage oil, clary sage oil, clove oil, cypress oil, eucalyptus oil, fennel oil, sea fennel oil, frankincense oil, geranium oil, ginger oil, grapefruit oil, jasmine oil, juniper oil, lavender oil, lemon oil, lemongrass oil, lime oil, mandarin oil, marjoram oil, myrrh oil, neroli oil, orange oil, patchouli oil, pepper oil, black pepper oil, petitgrain oil, pine oil, rose otto oil, rosemary oil, sandalwood oil, spearmint oil, spikenard oil, vetiver oil, wintergreen oil, and ylang ylang.

In certain instances, the non-volatile hydrocarbon-based oils are glyceride triesters and in particular to caprylic/capric acid triglycerides, synthetic esters and in particular isononyl isononanoate, oleyl erucate, $C_{12}$-$C_{15}$ alkyl benzoate, 2-ethylphenyl benzoate and fatty alcohols, such as octyldodecanol.

As volatile hydrocarbon-based oils, mention is made of hydrocarbon-based oils containing from 8 to 16 carbon atoms and in particular of branched $C_8$-$C_{16}$ alkanes, such as $C_8$-$C_{16}$ isoalkanes of petroleum origin (also known as isoparaffins), such as isododecane (also known as 2,2,4,4,6-pentamethylheptane), isodecane or isohexadecane, the oils sold under the Isopar or Permethyl trade names, branched C $C_8$-$C_{16}$ esters, and isohexyl neopentanoate.

The amount of oil, if present, may be in an amount of about 0.1 to about 10 wt. %, about 0.1 to about 8 wt. %, about 0.1 to about 6 wt. %, about 0.1 to about 5 wt. %, about 0.1 to about 4 wt. %, about 0.5 to about 10 wt. %, about 0.5 to about 8 wt. %, about 0.5 to about 6 wt. %, about 0.5 to about 5 wt. %, about 1 wt. % to about 10 wt. %, about 1 wt. % to about 8 wt. %, about 1 wt. % to about 6 wt. %, about 1 wt. % to about 5 wt. %, about 2 wt. % to about 10 wt. %, about 2 wt. % to about 8 wt. %, or about 3 wt. % to about 10 wt. %.

Active Agents

Heat-protective compositions according to the present disclosure can optionally further include active agents. Suitable active agents include, for example, anti-acne agents, antimicrobial agents, anti-inflammatory agents, analgesics, anti-erythemal agents, antiruritic agents, antiedermal agents, antipsoriatic agents, antifungal agents, skin protectants, vitamins, antioxidants, scavengers, antiirritants, antibacterial agents, antiviral agents, antiaging agents, protoprotection agents, hair growth enhancers, hair growth inhibitors, hair removal agents, antidandruff agents, anti-seborrheic agents, exfoliating agents, wound healing agents, anti-ectoparacitic agents, sebum modulators, immunomodulators, hormones, botanicals, moisturizers, astringents, cleansers, sensates, antibiotics, anesthetics, steroids, tissue healing substances, tissue regenerating substances, hydroxyalkyl urea, amino acids, peptides, minerals, ceramides, biohyaluronic acids, vitamins, skin lightening agents, self tanning agents, coenzyme Q10, niacinimide, capcasin, caffeine, and any combination of any of the foregoing.

Adjuvants

Heat-protective compositions according to the present disclosure can optionally include one or more adjuvants, such as pH adjusters, emollients, humectants, conditioning agents, moisturizers, chelating agents, propellants, rheology modifiers and emulsifiers such as gelling agents, colorants, fragrances, odor masking agents, UV stabilizer, preservatives, and any combination of any of the foregoing. Examples of pH adjusters include, but are not limited to, aminomethyl propanol, aminomethylpropane diol, triethanolamine, triethylamine, citric acid, sodium hydroxide, acetic acid, potassium hydroxide, lactic acid, and any combination thereof.

Suitable conditioning agents include, but are not limited to, cyclomethicone; petrolatum; dimethicone; dimethiconol; silicone, such as cyclopentasiloxane and diisostearoyl trimethylolpropane siloxy silicate; sodium hyaluronate; isopropyl palmitate; soybean oil; linoleic acid; PPG-12/saturated methylene diphenyldiisocyanate copolymer; urea; amodimethicone; trideceth-12; cekimonium chloride; diphenyl dimethicone; propylene glycol; glycerin; hydroxyalkyl urea; tocopherol; quaternary amines; and any combination thereof.

Suitable preservatives include, but are not limited to, chlorophenesin, sorbic acid, disodium ethylenedinitrilotetraacetate, phenoxyethanol, methylparaben, ethylparaben, propylparaben, phytic acid, imidazolidinyl urea, sodium dehydroacetate, benzyl alcohol, methylehloroisothiazolinone, methylisothiazolinone, and any combination thereof. The heat-protective composition generally contains from about 0.001% to about 20% by weight of preservatives, based on 100% weight of total heat-protective composition. In another aspect, the composition contains from about 0.1% to about 10% by weight of preservatives, based on 100% weight of total heat-protective composition.

The above lists are only examples and not limiting.

Implementation of the present disclosure is provided by way of the following examples. The examples serve to illustrate the technology without being limiting in nature.

Example 1

SPF Boosting and Water-Resistant Properties

The compositions in the table below were prepared and the SPF and Water Resistance were measured.

| Formula | Ingredients | SPF In Vitro | WR In Vitro (%) |
|---|---|---|---|
| A | UV Filter (15 wt. %)<br>Glyceryl stearate/PEG-100 stearate (emulsifier) (3 wt. %)<br>Phenoxyethanol (preservative) (0.7 wt. %)<br>Water q.s | 5 | N/A |
| B | Argilla (7.5 wt. %)<br>UV Filters (15 wt. %)<br>Glyceryl stearate/PEG-100 stearate (emulsifier) (3 wt. %)<br>Phenoxyethanol (preservative) (0.7 wt. %)<br>Water q.s | 29 | 103% |
| C | Montmorillonite (7.5 wt. %)<br>UV Filters (15 wt. %)<br>Glyceryl stearate/PEG-100 stearate (emulsifier) (3 wt. %)<br>Phenoxyethanol (preservative) (0.7 wt. %)<br>Water q.s | 28 | 93% |
| D | Laponite (7.5 wt. %)<br>UV Filters (15 wt. %)<br>Glyceryl stearate/PEG-100 stearate (emulsifier) (3 wt. %)<br>Phenoxyethanol (preservative) (0.7 wt. %)<br>Water q.s. | 32 | 25% |

The 15 wt. % of UV filters used in the above formulations contained the following specific amounts of five UV filters.

| Chemical Name | Approximate Ratio | Wt. % of UV Filter (Used in 7.5% Clay Formulations) |
|---|---|---|
| Homosalate | 3.6 | 6 |
| Ethylhexyl Salicylate | 1.1 | 1.8 |
| Octocrylene | 2.0 | 3.36 |
| Butyl Methoxydibenzoylmethane | 1.0 | 1.68 |
| Benzophenone-3 | 1.3 | 2.17 |
| TOTAL | N/A | 15 wt. % |

The SPF was measured using a Labsphere 2000S UV analyzer. Each formulation (1.8 mg sample per $cm^2$ substrate) was weighed out on the rough surface of a PMMA plate. The formulations were then evenly spread using a circular motion following by a horizontal spreading movement onto the plate. Then, the plates were left to dry for 15 minutes. After drying, the treated plates were analyzed using Labsphere. Each treated plate was subjected to 5 measurements.

Water resistance was measured after the SPF was measured, the treated PMMA plates were placed in a modified Agilent Dissolution Apparatus. The treated plates were submerged in water (25° C.) for 10 minutes, with the instrument stirring at 25 rpm. Upon completion, the treated plates were air dried for 30 minutes and reanalyzed using the Labsphere. The water resistance was defined as follows:

% Water resistance=(final SPF/initial SPF)×100.

Example 2

Heat Protection Properties

The following compositions were prepared and the stability, color, and the amount of heat protection were measured.

| Formula | Ingredients | ΔT* | Color |
|---|---|---|---|
| | (7.5 wt. % Clays and 15 wt. % UV Filters) | | |
| | None (Control) | 6.0° C. | N/A |
| E | Kaolin (7.5 wt. %)<br>Water q.s | 6.2° C. | off-white |
| F | Bentonite (7.5 wt. %)<br>Water q.s | 6.4° C. | yellow-orange |
| G | UV Filters (15 wt. %)<br>Glyceryl stearate/PEG-100 stearate (emulsifier)(3 wt. %)<br>Phenoxyethanol (preservative) (0.7 wt. %)<br>Water q.s | 5.9° C. | white |
| H | Kaolin (7.5 wt. %)<br>UV Filters (15 wt. %)<br>Glyceryl stearate/PEG-100 stearate (emulsifier)(3 wt. %)<br>Phenoxyethanol (preservative) (0.7 wt. %)<br>Water q.s | Phase separated (unstable) | peach |
| I | Bentonite (7.5 wt. %)<br>UV Filters (15 wt. %)<br>Glyceryl stearate/PEG-100 stearate (emulsifier)(3 wt. %)<br>Phenoxyethanol (preservative) (0.7 wt. %)<br>Water q.s | Phase separated (unstable) | off-white |
| J | Argilla (7.5 wt. %)<br>UV Filters (15 wt. %)<br>Glyceryl stearate/PEG-100 stearate (emulsifier)(3 wt. %)<br>Phenoxyethanol (preservative) (0.7 wt. %)<br>Water q.s | 4.6° C. | pink-beige |
| K | Montmorillonite (7.5 wt. %)<br>UV Filters (15 wt. %)<br>Glyceryl stearate/PEG-100 stearate (emulsifier)(3 wt. %)<br>Phenoxyethanol (preservative) (0.7 wt. %)<br>Water q.s | 4.9° C. | beige |
| L | Laponite (7.5 wt. %)<br>UV Filters (15 wt. %)<br>Glyceryl stearate/PEG-100 stearate (emulsifier)(3 wt. %)<br>Phenoxyethanol (preservative) (0.7 wt. %)<br>Water q.s. | 1.1° C. | white |
| | (3.5 wt. % Clays and 20 wt. % UV Filters) | | |
| | None (Control) | 6.0° C. | N/A |
| M | Laponite (20 wt. %)<br>Water q.s. | 0.5° C. | clear |
| N | Argilla (3.5 wt. %)<br>Glyceryl stearate/PEG-100 stearate (emulsifier)(3 wt. %)<br>UV Filters (20 wt. %)<br>Phenoxyethanol (preservative) (0.7 wt. %)<br>Water q.s | 4.7° C. | Off-white |
| O | Montmorillonite (3.5 wt. %)<br>Glyceryl stearate/PEG-100 stearate (emulsifier)(3 wt. %)<br>UV Filters (20 wt. %)<br>Phenoxyethanol (preservative) (0.7 wt. %)<br>Water q.s | 4.8° C. | Off-white |
| P | Laponite (3.5 wt. %)<br>Glyceryl stearate/PEG-100 stearate (emulsifier)(3 wt. %)<br>UV Filters (20 wt.)<br>Phenoxyethanol (preservative) (0.7 wt. %)<br>Water q.s | 2.8° C. | Off-white |

*ΔT represents the change in temperature of human skin after 5 seconds of hot air (60-80° C.) exposure The 15 wt. % and the 20 wt. % of UV filters used in the above formulations contained the following specific amounts of five UV filters (which are used in the same ratios to one another in both cases).

| Chemical Name | Approximate Ratio | Wt. % of UV Filter (Used in 7.5% Clay Formulations) | Wt. % of UV Filter (Used in 3.5% Clay Formulations) |
|---|---|---|---|
| Homosalate | 3.6 | 6 | 8.00 |
| Ethylhexyl Salicylate | 1.1 | 1.8 | 2.40 |
| Octocrylene | 2.0 | 3.36 | 4.48 |
| Butyl Methoxydibenzoylmethane | 1.0 | 1.68 | 2.24 |
| Benzophenone-3 | 1.3 | 2.17 | 2.89 |
| TOTAL | N/A | 15 wt. % | 20 wt. % |

Example 3

Heat-Protection Properties

| Phase | Chemical Name | L | G | H | I |
|---|---|---|---|---|---|
| A | Water | 73.79 | 81.29 | 73.79 | 73.79 |
|  | Laponite | 7.5 | 0 | 0 | 0 |
|  | Kaolin | 0 | 0 | 7.5 | 0 |
|  | Bentonite | 0 | 0 | 0 | 7.5 |
|  | Phenoxyethanol | 0.7 | 0.7 | 0.7 | 0.7 |
| B | Homosalate | 6 | 6 | 6 | 6 |
|  | Ethyl hexyl Salicylate | 1.8 | 1.80 | 1.8 | 1.8 |
|  | Octocrylene | 3.36 | 3.36 | 3.36 | 3.36 |
|  | Butyl Methoxydibenzoylmethane | 1.68 | 1.68 | 1.68 | 1.68 |
|  | Benzophenone-3 | 2.17 | 2.17 | 2.17 | 2.17 |
|  | Glyceryl Stearate/PEG-100 Stearate | 3 | 3 | 3 | 3 |
|  | Extreme Heat Protection | Yes | No | No | No |

Formulas 1-4 in the table above were prepared as follows: Phase A was mixed at room temperature using a high speed mixer (2500 rpm, 5 min). Separately, phase B was stirred and heated to 85° C. Phase B was then added to phase A, and mixed using a high speed mixer (2500 rpm, 5 min).

Formulations 1-4 were tested for their ability to protect skin from extreme heat. "Extreme heat" was generated using a hair drier (highest and hottest setting) for 10 seconds, approximately 2 inches from where product was applied on back of hand. The formulation was applied to the back of the hand to provide coverage of 2 mg/cm$^2$. It was applied and rubbed onto the back of the hand until the skin was uniformly coated. The temperature of the hair drier was 60-80° C. The initial temperature of the skin before heating and the temperature immediately after exposure to heat were measured using an infrared thermometer. First, the formulation was applied to the skin and the initial temperature of the coated skin was determined using an IR thermometer. Next, heat was applied to the back of the hand for 10 seconds. Immediately after the heat stimulus was terminated, the temperature was again measured with an IR thermometer. As shown in the table above, only the formulation containing laponite exhibited extreme heat protection.

As used herein, the terms "comprising," "having," and "including" are used in their open, non-limiting sense.

The terms "a," "an," and "the" are understood to encompass the plural as well as the singular.

The expression "at least one" means "one or more" and vice versa, and thus includes individual components as well as mixtures/combinations.

All ranges and values disclosed herein are inclusive and combinable. For examples, any value or point described herein that falls within a range described herein can serve as a minimum or maximum value to derive a sub-range, etc.

All publications and patent applications cited in this specification are herein incorporated by reference, and for any and all purposes, as if each individual publication or patent application were specifically and individually indicated to be incorporated by reference. In the event of an inconsistency between the present disclosure and any publications or patent application incorporated herein by reference, the present disclosure controls.

The invention claimed is:

1. A heat-protective composition comprising:
   2 to about 8 wt. % of laponite;
   about 0.1 to about 10 wt. % of one or more nonionic emulsifiers selected from the group consisting of a polyol ester, a glycerol ether, an oxyethylenated fatty alcohol ether, an oxyethylenated fatty acid ester, and a mixture thereof; and
   at 65 to about 85 wt. % water;
   wherein the weight percentages are based on the total weight of the heat-protective composition; the composition is an emulsion; the composition provides protection from heat when applied to skin and/or hair; and the composition is free of colorants.

2. The heat-protective composition of claim 1, further comprising:
   about 0.1 to about 30 wt. % of one or more UV filters.

3. The heat-protective composition of claim 2, wherein the one or more nonionic emulsifiers comprises a polyol ester, an oxyethylenated fatty acid ester, or a mixture thereof.

4. The heat-protective composition of claim 3, wherein the one or more nonionic emulsifiers comprises both a polyol ester and an oxyethylenated fatty acid ester.

5. The heat-protective composition of claim 4, wherein the one or more nonionic emulsifiers comprises a combination of glyceryl stearate and PEG-100 stearate.

6. The heat-protective composition of claim 1, wherein the amount of the one or more nonionic emulsifiers is about 0.1 wt. % to about 5 wt. %, based on the total weight of the heat-protective composition.

7. The heat-protective composition of claim 1, wherein application of at least 2.0 mg/cm$^2$ of the composition to the skin maintains the skin temperature at or below a threshold temperature of 40° C. for at least 10 seconds of exposure to heat flux of 40 kW/m$^2$.

8. The heat-protective composition of claim 1, wherein the laponite has an average particle size of about 5 to about 50 nm.

9. The heat-protective composition of claim 1, wherein the laponite has an average particle size of about 20 to about 30 nm.

10. The heat-protective composition of claim 1, further comprising:
    one or more film formers.

11. The heat-protective composition of claim 10, wherein the one or more film formers are selected from the group consisting of: sodium silicate, colloidal silica, pullulan, polycacrylate-21 (and) acrylates/dimethylaminoethylmethacrylate copolymer, polyurethanes, polysaccharides, polyvinylpyrrolidone, acrylates, and a mixture thereof.

12. The heat-protective composition of claim 11, wherein the one or more film formers comprises an acrylate/octylacrylamide copolymer.

13. The heat-protective composition of claim 1, further comprising:
    one or more preservatives.

14. The heat-protective composition of claim 13, wherein the one or more preservatives are selected from the group consisting of chlorophenesin, sorbic acid, disodium ethylenedinitrilotetraacetate, phenoxyethanol, methylparaben, ethylparaben, propylparaben, phytic acid, imidazolidinyl urea, sodium dehydroacetate, benzyl alcohol, methylehloroisothiazolinone, and methylisothiazolinone.

15. The heat-protective composition of claim 13, wherein the total amount of the one or more preservative is about 0.1% to about 10%, based on the total weight of the heat-protective composition.

16. A method for protecting skin from external thermal flux comprising applying the heat-protective composition of claim 1 to the skin.

17. A method for protecting hair from damage caused by heat comprising applying a heat-protective composition of claim 1 to the hair.

* * * * *